US00PP34249P2

(12) United States Plant Patent
Liu et al.

(10) Patent No.: US PP34,249 P2
(45) Date of Patent: May 17, 2022

(54) ***NELUMBO* PLANT NAMED 'ZHONGSHAN HONGLAN'**

(50) Latin Name: *Nelumbo nucifera*
Varietal Denomination: ZHONGSHAN HONGLAN

(71) Applicant: Institute of Botany, Jiangsu Province and Chinese Academy of Science, Nanjing (CN)

(72) Inventors: Xiaojing Liu, Nanjing (CN); Fengfeng Du, Nanjing (CN); Dongrui Yao, Nanjing (CN); Linhe Sun, Nanjing (CN); Jinfeng Li, Nanjing (CN)

(73) Assignee: Institute of Botany, Jiangsu Province and Chinese Acacemy of Science

( * ) Notice: Subject to any disclaimer, the term of this patent is extended or adjusted under 35 U.S.C. 154(b) by 0 days.

(21) Appl. No.: 17/554,683

(22) Filed: Dec. 17, 2021

(51) Int. Cl.
*A01H 6/00* (2018.01)
*A01H 5/02* (2018.01)

(52) U.S. Cl.
USPC ..... Plt./342

(58) Field of Classification Search
USPC ..... Plt./342
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Nelumbo* plant named 'ZHONGSHAN HONGLAN' is disclosed, characterized by multi-colored, multi-whorled flowers with red-purple tips, white centers, and yellow bases. Flowers have a bowl-shaped form, and grey-colored anthers. The new variety is useful as both an ornamental plant and for cut flower production.

3 Drawing Sheets

Latin name of the genus and species: *Nelumbo nucifera*.
Variety denomination: 'ZHONGSHAN HONGLAN'.

BACKGROUND OF THE INVENTION

The new cultivar, *Nelumbo* 'ZHONGSHAN HONGLAN', is the product of a planned breeding program. The new variety originated from a cross pollination of the unpatented, seed parent, *Nelumbo* 'Xin Yuhuaqing' with the pollen parent the unpatented *Nelumbo* 'Zhuoyue'. The cross pollination was made during July of 2018 in Nanjing, Jiangsu province, China at a research nursery. The new cultivar 'ZHONGSHAN HONGLAN' was selected in June of 2019 at the same location.

Asexual reproduction of the new cultivar 'ZHONGSHAN HONGLAN' was first performed by root division in Jiangsu province, China at a research nursery April of 2020. *Nelumbo* 'ZHONGSHAN HONGLAN' has since produced multiple generations and has shown that the unique features of this cultivar are stable and reproduced true to type.

SUMMARY OF THE INVENTION

The cultivar 'ZHONGSHAN HONGLAN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ZHONGSHAN HONGLAN'. These characteristics in combination distinguish 'ZHONGSHAN HONGLAN' as a new and distinct *Nelumbo* cultivar:

1. Multi-whorled flowers with many petals.
2. Multi-colored flower with a red-purple tip, white center, and yellow base.

3. Bowl-shaped flower form with a flatter top surface, and a more conspicuous receptacle.
4. Middle whorl petal tips bend inward.
5. Grey anther color.
6. Flowers from mid-June to late August.

PARENTAL COMPARISON

Plants of the new cultivar 'ZHONGSHAN HONGLAN' are similar to plants of the seed parent in most horticultural characteristics. However, plants of the new cultivar 'ZHONGSHAN HONGLAN' differ in the following:

1. 'ZHONGSHAN HONGLAN' produces fewer petals per flower than the seed parent.
2. Flower color of 'ZHONGSHAN HONGLAN' is a deeper red-purple at the tip, and a brighter yellow base than the flower color of the seed parent.
3. Flower form of 'ZHONGSHAN HONGLAN' is flatter on the top surface, with a more conspicuous receptacle; the flower form of the seed parent is bowl-shaped with a normal-sized receptacle.
4. 'ZHONGSHAN HONGLAN' has a much higher number of stamens than the seed parent.
5. 'ZHONGSHAN HONGLAN' has grey colored anthers, while the seed parent has yellow anthers.
6. 'ZHONGSHAN HONGLAN' has a white staminal appendage, while the seed parent has a pale yellow staminal appendage.

Plants of the new cultivar 'ZHONGSHAN HONGLAN' are similar to the pollen parent in most horticultural characteristics. However, plants of the new cultivar 'ZHONGSHAN HONGLAN' differ in the following:

1. 'ZHONGSHAN HONGLAN' produces flowers with a red-purple tip, white center, and yellow base; the pollen parent produces flowers with a red-purple tip, red-purple center, and yellow base.

2. Flower form of 'ZHONGSHAN HONGLAN' is flatter on the top surface, with a more conspicuous receptacle; the flower form of the pollen parent is cup-shaped with a normal-sized receptacle.
3. Flowers of 'ZHONGSHAN HONGLAN' have middle layer petal tips bending inward; middle layer petal tips of the pollen parent are rounded.
4. 'ZHONGSHAN HONGLAN' has a higher number of stamens than the pollen parent.
5. 'ZHONGSHAN HONGLAN' has grey colored anthers, while the pollen parent has yellow anthers.

COMMERCIAL COMPARISON

The new cultivar 'ZHONGSHAN HONGLAN' can be compared to the unpatented commercial variety *Nelumbo* 'Jinling Nvshen'. Plants of the new cultivar 'ZHONGSHAN HONGLAN' differ in the following:

1. Flowers of 'ZHONGSHAN HONGLAN' have fewer petals than flowers of 'Jinling Nvshen'.
2. Flower form of 'ZHONGSHAN HONGLAN' is flatter on the top surface, with a more conspicuous receptacle; the flower form of 'Jinling Nvshen' is plate-shaped with a normal-sized receptacle.
3. Flowers of 'ZHONGSHAN HONGLAN' have middle layer petal tips bending inward; middle layer petal tips of this comparator are rounded.
4. 'ZHONGSHAN HONGLAN' has grey colored anthers, while this comparator has yellow anthers.

BRIEF DESCRIPTION OF THE PHOTOGRAPHS

The accompanying photographs illustrate in full color typical plants of 'ZHONGSHAN HONGLAN' grown outdoors, in the ground in Jingsu Province, China. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Nelumbo* plant. Temperatures ranged from approximately 13° C. to 28° C. night and about 16° C. to 34° C. during the day. No artificial light, photoperiodic treatments or chemical treatments were given to the plants.

DETAILED BOTANICAL DESCRIPTION

Figure 1:
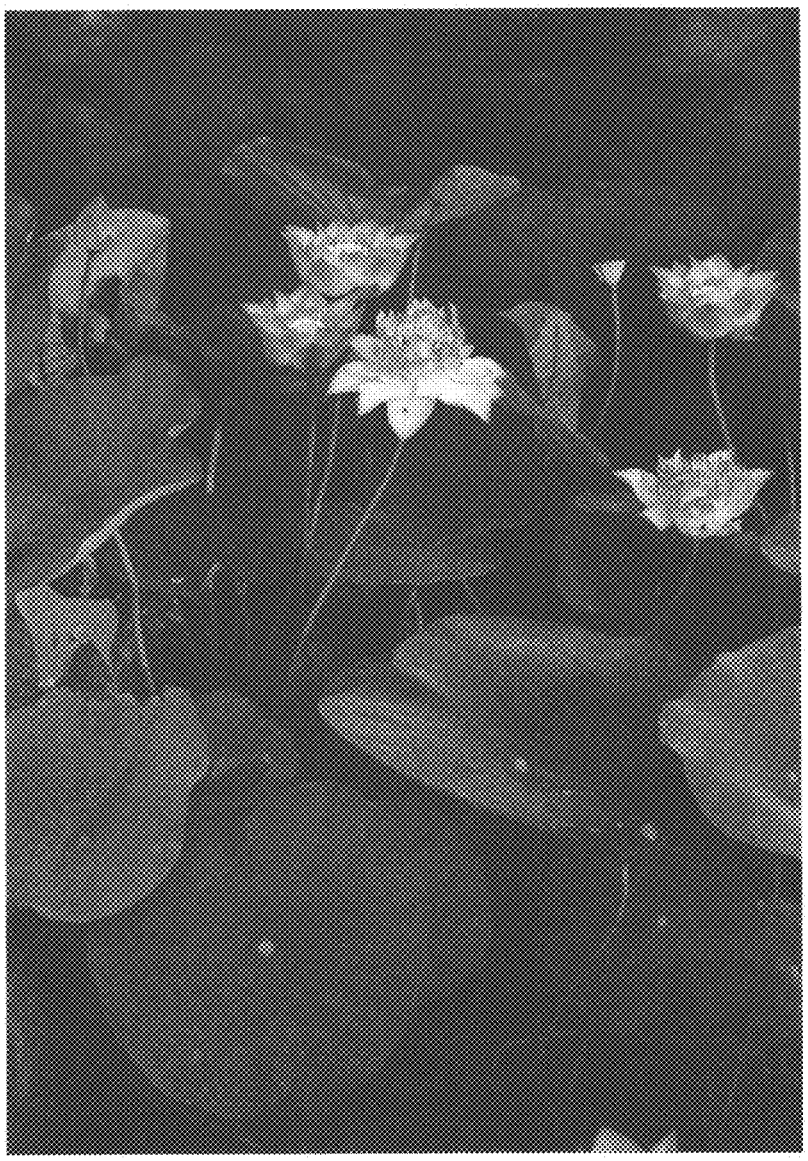
FIG. 1 illustrates in full color typical flowering plants of *Nelumbo* 'ZHONGSHAN HONGLAN' at approximately 1 year of age.
Figure 2:
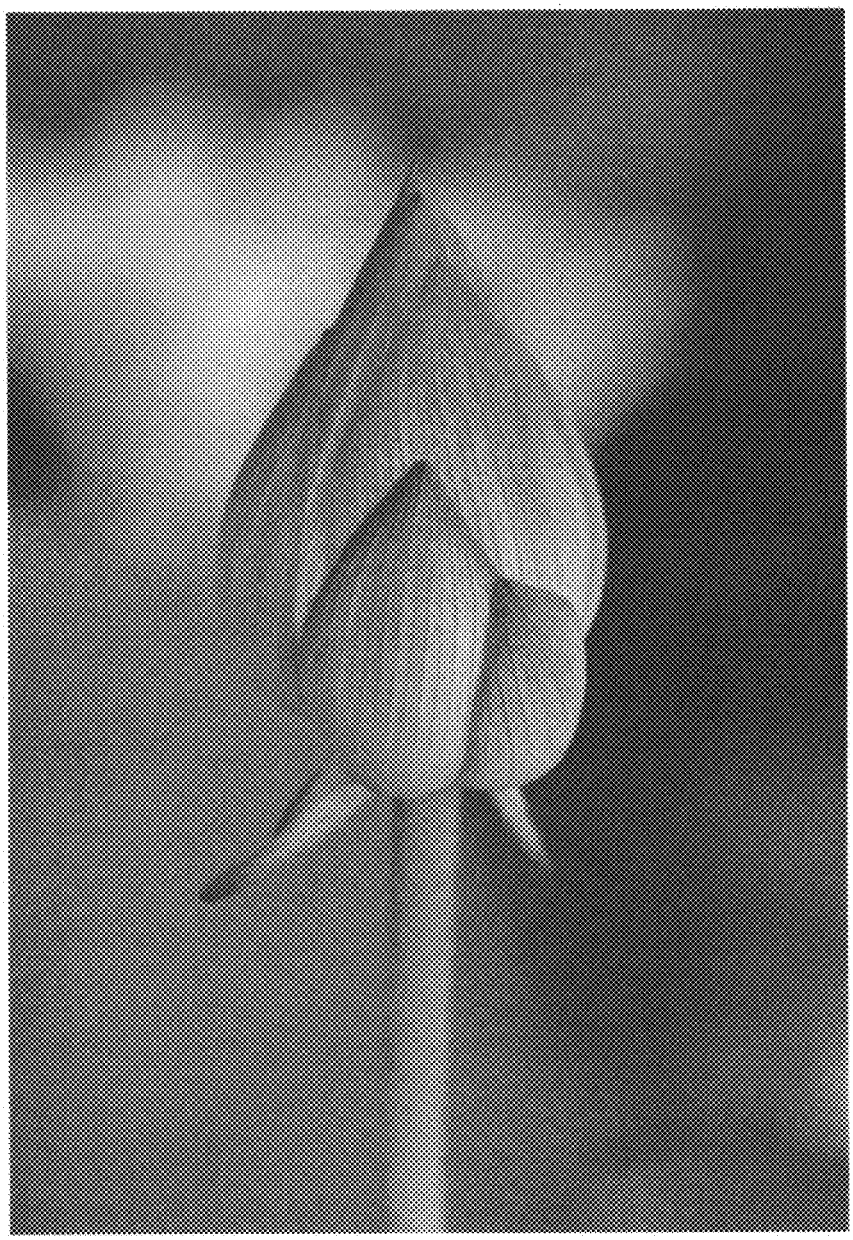
FIG. 2 illustrates in full color a typical flower bud of *Nelumbo* 'ZHONGSHAN HONGLAN'.
Figure 3:
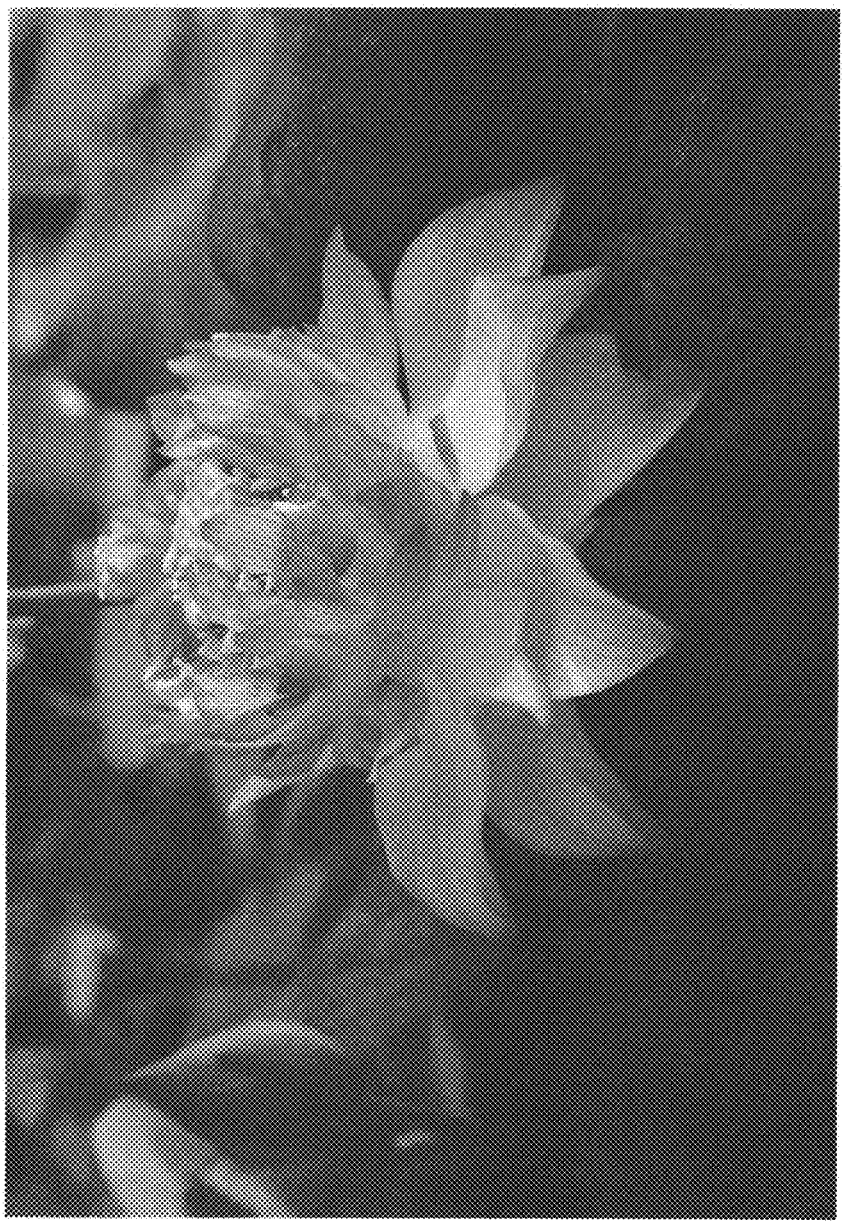
FIG. 3 illustrates in full color a typical open flower of *Nelumbo* 'ZHONGSHAN HONGLAN'.

In the following description, color references are made to The Royal Horticultural Society Colour Chart, 2019, except where general terms of ordinary dictionary significance are used. The following observations and measurements describe 'ZHONGSHAN HONGLAN' plants grown in an outdoor pond in Jiangsu Province, China. Average day temperature range was around 25° C. to 38° C.; average night temperature ranged around 20° C. to 30° C. No artificial light, photoperiodic treatments or chemical treatments were given to the plants. Natural light conditions were full sunlight. Measurements and numerical values represent averages of typical plant types. Measurements were taken during June to August of 2021.

Botanical classification: *Nelumbo nucifera* 'ZHONGSHAN HONGLAN'.

PROPAGATION

Type of propagation typically used: Root divisions.

Root description: Adventitious roots at the rhizome node. Moderately dense, moderately branching, medium thickness, fleshy texture. White in color, not accurately described with R.H.S. chart.

PLANT

Age of plant described: Approximately 4 months.

Container size of the plant described: In a pond of approximately 2 meters in length, 0.9 meters in width, and 25 cm in depth.

Growth habit: Heliophilous.

Height: Average 45 to 85 cm from soil to top of foliar plat 61 to 99 cm from soil to top of floral plane.

Plant spread: Approximately 100×90 cm.

Growth rate: Moderate.

Plant vigor: High.

Branching habit: Sympodial.

Primary branches per plant: 5 to 10.

Secondary branches per primary lateral branch: 3 to 5.

Lateral branch length: 60 to 110 cm.

Lateral branch diameter: 2 to 3.2 cm.

Internode length: 11 to 15 cm.

Stem:

*Shape/appearance*.—Rhizome, nodose, cylindrical.

*Aspect*.—Horizontal underground growth.

*Strength*.—Weak.

*Color*.—Developing: Near RHS Yellow-White 158C. At Internodes: Near RHS Yellow-White 158C. Developed: Near RHS Greyed-Yellow 162C.

*Pubescence*.—None.

*Luster*.—Matte.

FOLIAGE

Leaf:

*Arrangement*.—Single leaf ranked, before and after flowering.

*Average length*.—Average 31 to 46 cm.

*Average width*.—28 to 38 cm.

*Shape of blade*.—Orbicular.

*Apex*.—Dimple.

*Base*.—Peltate.

*Margin*.—Entire, slightly undulate.

*Texture of top surface*.—Smooth.

*Texture of bottom surface*.—Smooth, cancellate.

*Color*.—Young foliage upper side: RHS Yellow-Green 147B. Young foliage, under side: RHS Yellow-Green 147C. Mature foliage upper side: RHS Green 137B. Mature foliage, under side: RHS Green 137A. Fall foliage upper side: RHS Yellow-Green N151D, centrally blotched Green 137B. Fall foliage, under side: RHS Yellow-Green N148D streaked Green 137A.

*Venation*.—Type: Reticulate. Venation color upper side: RHS Yellow-Green 148D. Venation color under side: RHS Yellow-Green 147D.

Petiole:
*Average length.*—Average range 43 cm to 69 cm.
*Average diameter.*—Average range 0.5 mm to 0.9 cm.
*Color.*—Upper surface: Yellow-Green 144C. Lower surface: Yellow-Green 144C.
*Texture.*—Semi-woody, slightly hirsute.
*Strength.*—Stiff.
*Interior.*—Mostly hollow with moderate latex.

FLOWER

Natural flowering season: June through August.
Flower type and habit: Single, double-layered flowers. Upright. Bowl-shaped. Freely flowering habit.
Flowers per plant: 12 to 22 flowers and buds per square meter produced per year.
Flower longevity on plant: 5 to 6 days. Self-cleaning.
Flower longevity as a cut flower: 3 to 4 days.
Flower size:
*Height.*—Approximately 15 to 19 cm.
*Width.*—Approximately 15 to 19 cm.
*Depth.*—5.8 to 7 cm.
Bud:
*Shape.*—Oval.
*Length.*—Approximately 5.5 to 6.5 cm.
*Diameter.*—Approximately 3.2 to 4.4 cm.
*Luster.*—None.
*Color.*—Upper: Base near Yellow-Green 144D. Upper 75% very heavy Red-Purple 71A flush over 144D. Veins strong Greyed-Purple N186D. Margins Red-Purple 70A.
Petals:
*Arrangement.*—Verticillate.
*Quantity.*—86 to 92.
*Number of whorls.*—8.
*Fused.*—No.
*Margin.*—Entire.
*Shape.*—Obovate.
*Apex.*—Acuminate.
*Base.*—Truncate.
*Texture.*—Papery, both surfaces.
*Rugosity.*—Smooth and weak, under side only.
*Luster.*—Weak, both sides.
*Petal length.*—3.1 to 8 cm.
*Petal width.*—1 to 5.2 cm.
*Color.*—When Opening: Upper Surface: Tip: RHS Red-Purple 59C; Middle: White N155B; Base: Yellow 3B. Under Surface: Tip: RHS Red-Purple 59C; Middle: White N155B, clearly veins; Base: Yellow 4B. Fully Opened: Upper Surface: Tip: RHS Red-Purple 58A; Middle: White 155D; Base: Yellow 3B. Under Surface: Tip: RHS Red-Purple 58A; Middle: White N155C, Venation: Red-Purple 59C; Base: Yellow 4B. Upper Surface: Tip: RHS Red-Purple 59D; Middle: Yellow 4D; Base: Green-Yellow 1D. Under Surface: Tip: RHS Red-Purple 59D; Middle: Yellow 4D, clearly veins; Base: Green-Yellow 2D.
Petaloids:
*Arrangement.*—Verticillate.
*Quantity.*—72 to 78.
*Number of whorls.*—4.
*Length.*—3.1 to 5.4 cm.
*Width.*—1 to 1.8 cm.
*Shape.*—Obovate to lanceolate.
*Margin.*—Entire.
*Apex.*—Acuminate.
*Base.*—Wedge.
*Texture.*—Papery, both surfaces.
*Rugosity.*—Smooth and weak, under side.
*Luster.*—Weak, both sides.
*Color.*—When opening: Upper surface: Upper: RHS Red-Purple 59C; Base: Yellow 3A. Under surface: Upper: RHS Red-Purple 59C, clearly veins; Base: Yellow 3B. Fully opened: Upper surface: Upper: RHS Red-Purple 60B; Venation: Red-Purple 59C; Base: Yellow 4A. Under surface: Upper: RHS Red-Purple 60B; Venation: Red-Purple 59C; Base: Yellow 2B. Fading: Upper surface: Upper: RHS Red-Purple 59D; Base: Yellow 2C. Under surface: Upper: RHS Red-Purple 59D, clearly veins; Base: Yellow 3D.
Sepals:
*Quantity.*—8.
*Arrangement.*—Verticillate.
*Calyx shape.*—Oval.
*Fused.*—No.
*Number of whorls.*—2.
*Length.*—1 to 5.8 cm.
*Width.*—0.6 to 2.3 cm.
*Shape.*—Ovoid.
*Apex.*—Acuminate.
*Margin.*—Entire.
*Base.*—Truncate.
*Texture.*—Papery, both sides.
*Luster.*—Weak, both sides.
*Color.*—When Opening: Upper Surface: Upper: RHS Red-Purple 59C; Base: White N155C. Under Surface: Upper: RHS Red-Purple 59C; Base: Yellow-Green N144D. Fully Opened: Upper Surface: Upper: RHS Red-Purple 60B; Base: White N155D. Under Surface: Upper: RHS Red-Purple 60B; Base: Yellow-Green N144D.
Fragrance: Moderate.
Pedicel:
*Length.*—Average 56 to 93 cm.
*Diameter.*—Average 7 to 8 mm.
*Strength.*—Medium, stout.
*Texture.*—Semi-woody, stiff, inside vertical hollow and latex.
*Luster.*—Weak.
*Color.*—RHS Yellow-Green 146C.

REPRODUCTIVE ORGANS

Stamens: (Androecium).
*Number.*—Average 164 to 196.
*Filament length.*—Approximately 13 to 14 mm.
*Filament color.*—Yellow 2D.
*Anther length.*—8 to 9 mm.
*Anther width.*—1 to 1.5 mm.
*Anther color.*—Greyed-Green 196A.
*Anther shape.*—Bar.
*Pollen.*—None.
Pistil: (Gynoecium).
*Number.*—Average range 14 to 23.
*Length.*—Average 10 to 20 mm.

*Stigma*.—Shape: Circular. Color: Yellow 4A. Style Length: 1 to 2 mm. Style Color: Yellow-White 158D. Ovary Color: Yellow-White 158D.

OTHER CHARACTERISTICS

Seeds: 7 to 13 per flower.
*Length*.—15 to 17 mm.
*Diameter*.—9 to 12 mm.
*Texture*.—Nut, smooth.
*Color*.—Near RHS Brown 200A.
Fruit: 24 to 44 per plant.
*Length*.—3.1 to 4.5 cm.
*Diameter*.—3.4 to 9.3 cm.
*Texture*.—Smooth.
*Color*.—Near RHS Yellow-Green N144B, turning N144B then near Grey-Brown N199C.
*Taste*.—None.
*Days to ripen*.—21 to 40 days.
Temperature tolerance: Tolerates temperatures from approximately −10° C. to at least 40° C.
Disease/pest resistance: Neither resistance nor susceptibility to normal diseases and pests of *Nelumbo* observed.

What is claimed is:

1. A new and distinct cultivar of *Nelumbo* plant named 'ZHONGSHAN HONGLAN' as herein illustrated and described.

* * * * *